US011583168B2

(12) United States Patent
Viren

(10) Patent No.: US 11,583,168 B2
(45) Date of Patent: Feb. 21, 2023

(54) ENDOTRACHEAL TUBE SYSTEM AND METHOD

(71) Applicant: Thomas J. Viren, Bovey, MN (US)

(72) Inventor: Thomas J. Viren, Bovey, MN (US)

( * ) Notice: Subject to any disclaimer, the term of this patent is extended or adjusted under 35 U.S.C. 154(b) by 656 days.

(21) Appl. No.: 16/184,981

(22) Filed: Nov. 8, 2018

(65) Prior Publication Data

US 2020/0147331 A1 May 14, 2020

(51) Int. Cl.
| | |
|---|---|
| *A61B 1/00* | (2006.01) |
| *A61M 16/04* | (2006.01) |
| *A61B 1/267* | (2006.01) |
| *A61B 1/012* | (2006.01) |
| *A61B 1/07* | (2006.01) |
| *A61B 1/04* | (2006.01) |

(Continued)

(52) U.S. Cl.
CPC .......... *A61B 1/00135* (2013.01); *A61B 1/012* (2013.01); *A61B 1/044* (2022.02); *A61B 1/07* (2013.01); *A61B 1/2673* (2013.01); *A61M 16/0418* (2014.02); *A61M 16/0434* (2013.01); *A61M 16/0488* (2013.01); *A61M 25/0054* (2013.01); *A61M 25/09* (2013.01)

(58) Field of Classification Search
CPC ......... A61B 1/2673; A61B 1/012; A61B 1/07; A61B 1/00082; A61B 1/0684; A61B 1/0676; A61B 1/00135; A61B 1/05; A61B 5/285; A61B 1/0055; A61B 1/0056; A61B 1/0051; A61B 1/0057; A61M 16/04; A61M 16/0054; A61M 16/0418; A61M 16/0486; A61M 16/0488; A61M 16/0434; A61M 25/09; A61M 16/0816; A61M 2205/0283; A61M 2205/587; A61M 2205/3592; A61M 25/0147; A61M 25/0138
See application file for complete search history.

(56) References Cited

U.S. PATENT DOCUMENTS

| | | | | |
|---|---|---|---|---|
| 4,150,676 A | * | 4/1979 | Jackson | A61M 16/04 128/207.18 |
| 4,584,998 A | * | 4/1986 | McGrail | A61M 16/042 128/207.15 |

(Continued)

OTHER PUBLICATIONS

Medline Industries, Inc., MLK86349H—Endotrol O / N Dual Cuffed Trach Tubes by Medtronic, https://www.medline.com/sku/item/MDPMLK86349H?skuIndex=P1S2&question=endotrol&flowType=search&indexCount=1#, p. 1.

*Primary Examiner* — Timothy J Neal
(74) *Attorney, Agent, or Firm* — Allison Johnson, P.A.

(57) ABSTRACT

An endotracheal tube includes a main tubular portion including a distal end and a proximal end opposite the distal end, the main tubular portion including a central lumen at least in part defined by a wall of the main tubular portion; a wire lumen disposed within the wall of the main tubular portion, the wire lumen defined at least in part by a sidewall portion of the wire lumen and extending from about the proximal end of the main tubular portion to about the distal end of the main tubular portion; a wire disposed in the wire lumen; and one or more cutouts extending along a portion of the wall of the main tubular portion, the cutouts comprising openings in the sidewall portion of the wire lumen, wherein the cutouts are not in fluid communication with the central lumen.

22 Claims, 5 Drawing Sheets

(51) Int. Cl.
*A61M 25/00* (2006.01)
*A61M 25/09* (2006.01)

(56) References Cited

U.S. PATENT DOCUMENTS

| | | | | |
|---|---|---|---|---|
| 4,589,410 | A * | 5/1986 | Miller | A61M 16/04 |
| | | | | D24/129 |
| 4,685,457 | A * | 8/1987 | Donenfeld | A61M 16/0418 |
| | | | | 128/207.14 |
| 5,304,131 | A * | 4/1994 | Paskar | A61M 25/0138 |
| | | | | 604/95.04 |
| 5,327,881 | A | 7/1994 | Greene | |
| 5,400,771 | A * | 3/1995 | Pirak | A61B 1/042 |
| | | | | 128/207.14 |
| 6,539,942 | B2 * | 4/2003 | Schwartz | A61M 16/0488 |
| | | | | 128/207.14 |
| 7,921,847 | B2 | 4/2011 | Totz | |
| 8,863,746 | B2 | 10/2014 | Totz | |
| 2002/0013547 | A1* | 1/2002 | Paskar | A61M 25/0152 |
| | | | | 604/95.04 |
| 2002/0043266 | A1* | 4/2002 | Toti | A61M 16/0434 |
| | | | | 128/207.14 |
| 2002/0096177 | A1* | 7/2002 | Toti | A61M 16/0418 |
| | | | | 128/200.26 |
| 2004/0181136 | A1* | 9/2004 | McDaniel | A61M 25/0138 |
| | | | | 600/374 |
| 2008/0287741 | A1* | 11/2008 | Ostrovsky | A61M 25/0147 |
| | | | | 600/141 |
| 2009/0125002 | A1* | 5/2009 | Totz | A61J 15/0003 |
| | | | | 604/528 |
| 2011/0004157 | A1* | 1/2011 | Dewaele | A61B 1/01 |
| | | | | 604/95.01 |
| 2011/0265798 | A1* | 11/2011 | Maguire | A61M 16/04 |
| | | | | 128/207.14 |
| 2014/0041665 | A1* | 2/2014 | Hwang | A61M 16/04 |
| | | | | 128/207.14 |
| 2015/0096556 | A1* | 4/2015 | Marks | A61M 16/0488 |
| | | | | 128/207.14 |
| 2015/0099997 | A1* | 4/2015 | Cabiri | A61B 17/00234 |
| | | | | 600/585 |
| 2015/0101442 | A1* | 4/2015 | Romo | A61B 1/0055 |
| | | | | 74/490.04 |
| 2016/0256230 | A1* | 9/2016 | Kowshik | A61B 34/30 |
| 2017/0203075 | A1* | 7/2017 | Yan | A61M 16/0493 |
| 2017/0232216 | A1* | 8/2017 | Nave | A61B 1/012 |
| | | | | 600/120 |
| 2018/0028779 | A1* | 2/2018 | von Oepen | A61F 2/2427 |
| 2019/0091444 | A1* | 3/2019 | Melsheimer | A61M 25/0136 |
| 2019/0117937 | A1* | 4/2019 | Humphrey | A61M 25/0136 |
| 2020/0139082 | A1* | 5/2020 | Matlock | A61M 25/0147 |
| 2020/0330729 | A1* | 10/2020 | Petitpierre | A61M 25/0133 |
| 2020/0337683 | A1* | 10/2020 | Meduri | A61B 1/0052 |
| 2020/0367722 | A1* | 11/2020 | Perez-Lizano | A61B 1/0051 |
| 2021/0015349 | A1* | 1/2021 | Okada | A61B 1/018 |

* cited by examiner

ENDOTRACHEAL TUBE SYSTEM AND METHOD

FIELD OF THE DISCLOSURE

The invention relates generally to an endotracheal tube system and method.

BACKGROUND

Endotracheal intubation can be one of the most critical and life-saving procedures performed in the pre-hospital and emergency room settings. The few critical minutes spent during endotracheal tube placement can be very chaotic and stressful.

Prior procedure for placing an endotracheal tube requires the intubating provider to gather and open a minimum of three pieces of equipment: an endotracheal tube, a stylet, and a syringe to inflate a cuff proximate the distal end of the endotracheal tube. Also required is the use of a device to visualize the vocal chords. Further, a chest x-ray also typically is performed—with a radiologist reading the x-ray—to confirm the placement of the endotracheal tube. Such prior procedure is both cumbersome and costly.

For example, the stylet is a stiff wire that is inserted into the lumen of the endotracheal tube. The stylet is placed to give the endotracheal tube the stiffness required so that the tube can be pushed through the oral, or nasopharyngeal cavity, and through the vocal cords. Typically, the intubating provider is required to bend the stylet into a desired shape. Often the intubating provider manipulates the patient to obtain a direct view of the vocal cords using a laryngoscope. Video enabled intubation devices do not require as much manipulation of the patient. The stylet shape can vary from a hockey stick shape used when direct visualization of the vocal cords are used, or a more acute and curved shape when video devices are used. Thus, depending on the intubating device used, the provider may need different shapes stylets, or one that can take on different shapes.

Thus, there remains a need for an improved endotracheal tube system and method.

SUMMARY

The present disclosure provides an endotracheal tube system and method that greatly enhances the ability of providers to intubate patients. In one exemplary embodiment, an endotracheal tube eliminates the need for use of a stylet to make the tube rigid enough to pass through the vocal chords. The endotracheal tube may include a stiffening mechanism and manipulable distal tip. In another embodiment, the endotracheal tube may be adjustable so that a preferred shape for insertion/placement may be obtained.

In another exemplary embodiment, an endotracheal tube eliminates the need to use a separate device to visualize the vocal chords. Patients are manipulated less. A video system, e.g., including a camera or fiber optics, imbedded within the body of the tube may be used to visualize endotracheal tube placement. Using a separate monitor, e.g., preferably connected via Bluetooth or wi-fi, views of the trachea down to the coryna and both main stem bronchi would be available. This is an improvement over current intubating devices that only give a view down to the vocal cords, and not these deeper structures. Also currently the video device is removed once the tube is placed. With this device a camera would be left in place, which would aid if it were necessary to reconfirm tube placement, and to aid nursing and respiratory therapy staff in suctioning the patient.

The above exemplary embodiments, either alone or in combination, thus streamline the process of endotracheal intubation and reduce costs. The time from decision to intubate to intubation may be decreased. First pass success may become more common, and patient outcomes may be improved.

Other benefits and advantages of the present disclosure will be appreciated from the following detailed description.

DETAILED DESCRIPTION

Embodiments of the invention and various alternatives are described. Those skilled in the art will recognize, given the teachings herein, that numerous alternatives and equivalents exist which do not depart from the invention. It is therefore intended that the invention not be limited by the description set forth herein or below.

One or more specific embodiments of the system and method will be described below. These described embodiments are only exemplary of the present disclosure. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Further, for clarity and convenience only, and without limitation, the disclosure (including the drawings) sets forth exemplary representations of only certain aspects of events and/or circumstances related to this disclosure. Those skilled in the art will recognize, given the teachings herein, additional such aspects, events and/or circumstances related to this disclosure, e.g., additional elements of the devices described; events occurring related to endotracheal tube insertion/placement; etc. Such aspects related to this disclosure do not depart from the invention, and it is therefore intended that the invention not be limited by the certain aspects set forth of the events and circumstances related to this disclosure.

Figure 1A:
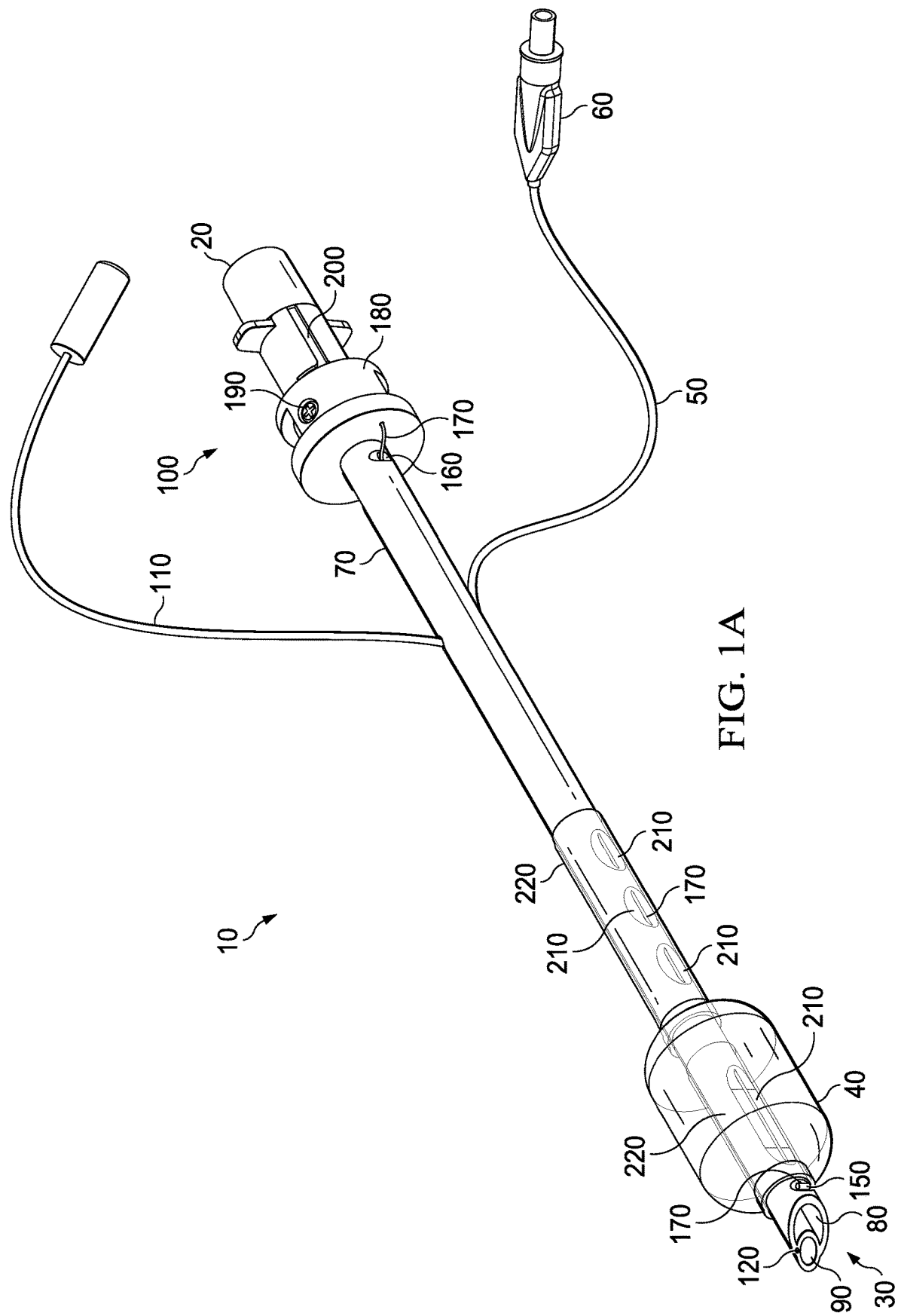
FIG. 1A is a perspective view of an exemplary embodiment of an endotracheal tube system
Figure 1B:
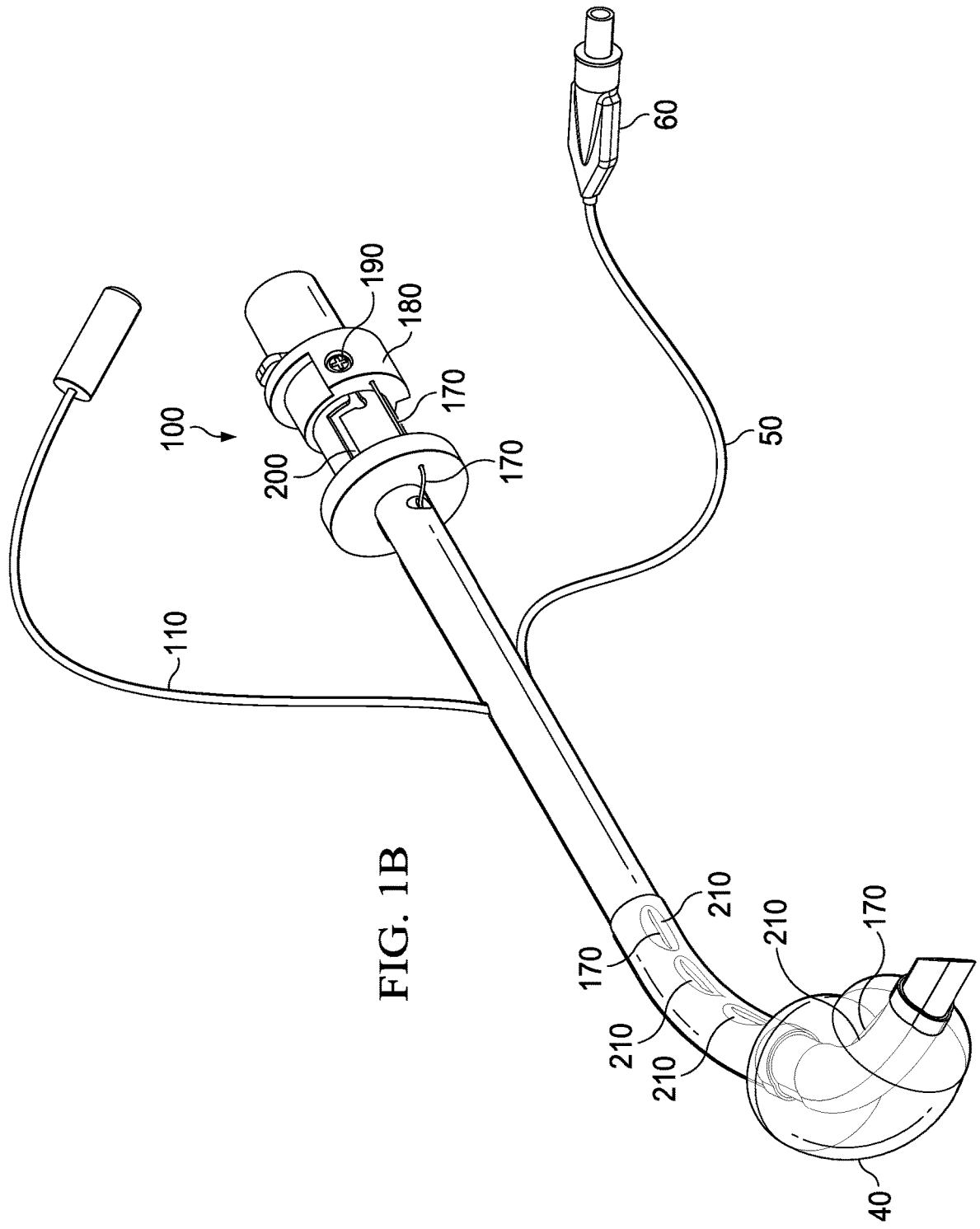
FIG. 1B is a perspective view of the exemplary embodiment of an endotracheal tube system shown in FIG. 1, with its shape adjusted by way of example only.
Figure 2:
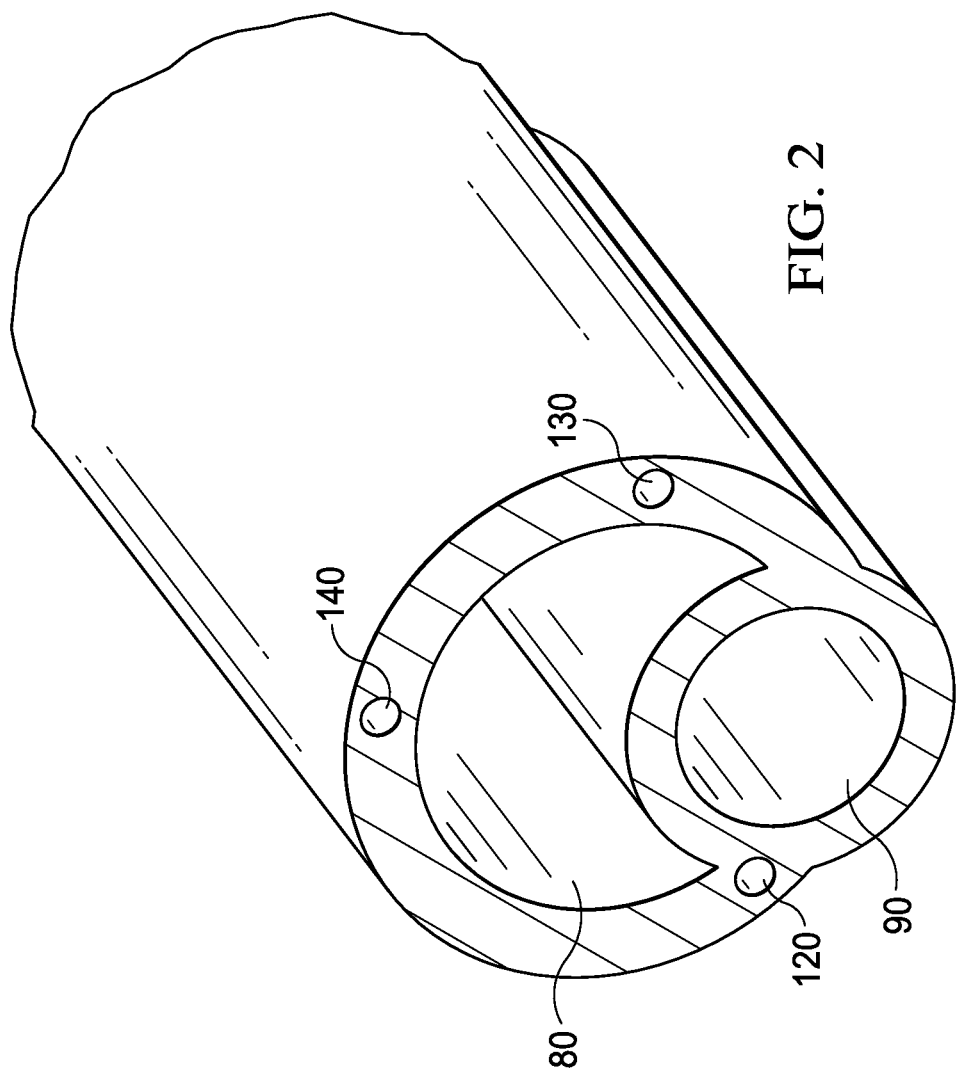
FIG. 2 is a perspective cross sectional view of the exemplary embodiment of an endotracheal tube system shown in FIG. 1.
Figure 3:
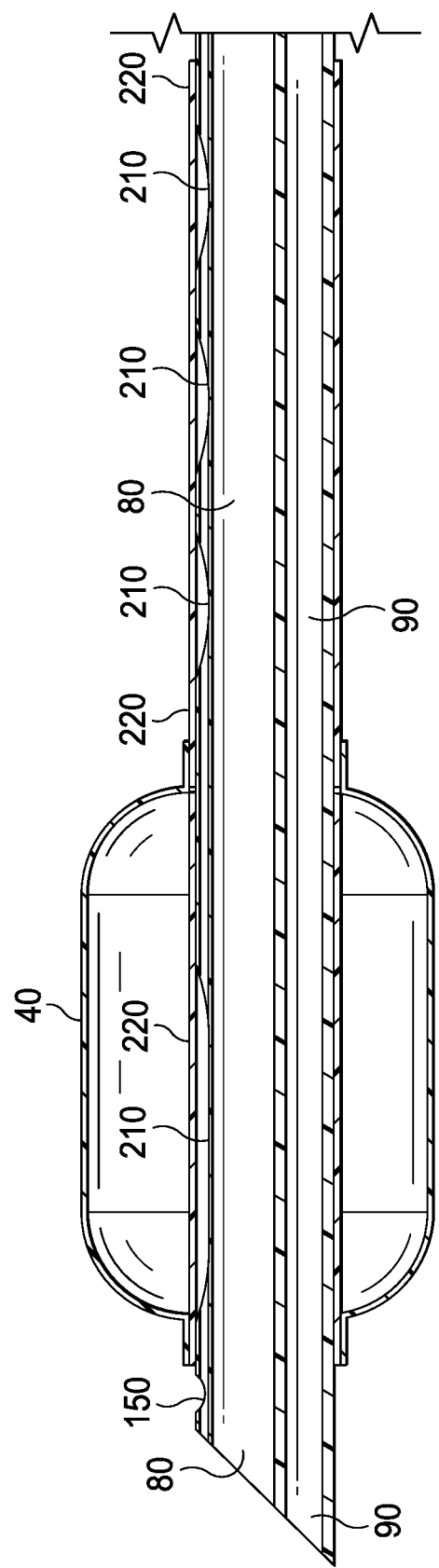
FIG. 3 is a cross sectional view of the distal portion of the exemplary embodiment of an endotracheal tube system shown in FIG. 1.

Turning now to the drawings, an exemplary endotracheal tube system is shown in FIG. 1A. The endotracheal tube 10 includes a proximal end 20 and a distal end 30. A balloon or cuff 40 is disposed proximate the distal end of the tube 10. The cuff 40 is inflated via airway 50. Airway 50 includes a balloon connector 60 on its proximal end for connection to a bulb syringe used to inflate the cuff 40. The connector 60 also includes a one-way valve to hold the air in the cuff 40 and keep the cuff 40 inflated. Airway 50 runs along the length of the tube 10 within the lumen 130 disposed in the wall of the tube 10. See FIG. 2. Airway 50 has a distal end of the lumen 130 disposed within the cuff 40, so as to form a continuous fluid pathway between the supply of air and the interior of the cuff 40.

The tube 10 includes a main tubular portion 70 having a central lumen 80 therethrough. A second lumen 90 also may be provided through the tube 10 in some embodiments. The second lumen 90 may house optical components such as wiring or fiber optic cables. A small camera may be positioned at the distal tip of the tube 10 to provide a video feed. Turning on the feed may result, for example, by activating a switch, e.g., by hand or with rotation of at least a portion of the hub 100. Advantageously, wi-fi or Bluetooth connection to a separate monitor is provided via the hub 100. Alternately, wires and/or standard fiber optic connection elements may be used.

Line 110 may connect to a source of air at its proximal end. The air may travel to the distal tip of tube 10 via lumen 120 disposed within a sidewall of tube 10. The air delivered via lumen 120 may be used to clear fluids or debris at the distal tip of the tube 10 from the camera or optical components housed in lumen 90. In one embodiment, air may be delivered using the same syringe used to inflate cuff 40.

A third lumen 140 may run in the wall of tube 10 from a distal end 150 proximate the distal end 30 of tube 10 to a proximal end 160 disposed proximate the hub 100. A wire 170 may be disposed within lumen 140 and may extend between the hub 100 and the distal tip 30 of tube 10. The wire 170 at its first distal end may be secured to tube 10 at end 150 of lumen 140. The wire 170 at its second proximal end may be secured to collar 180 of hub 100. The collar 180 may move along the length of the hub 100. A pin or screw 190 which extends radially through collar 180 may have an end disposed in a channel 200 formed in hub 100. The channel 200 thus controls the movement of collar 180 along a particular desired path corresponding to the shape of the channel 200.

Figure 4:
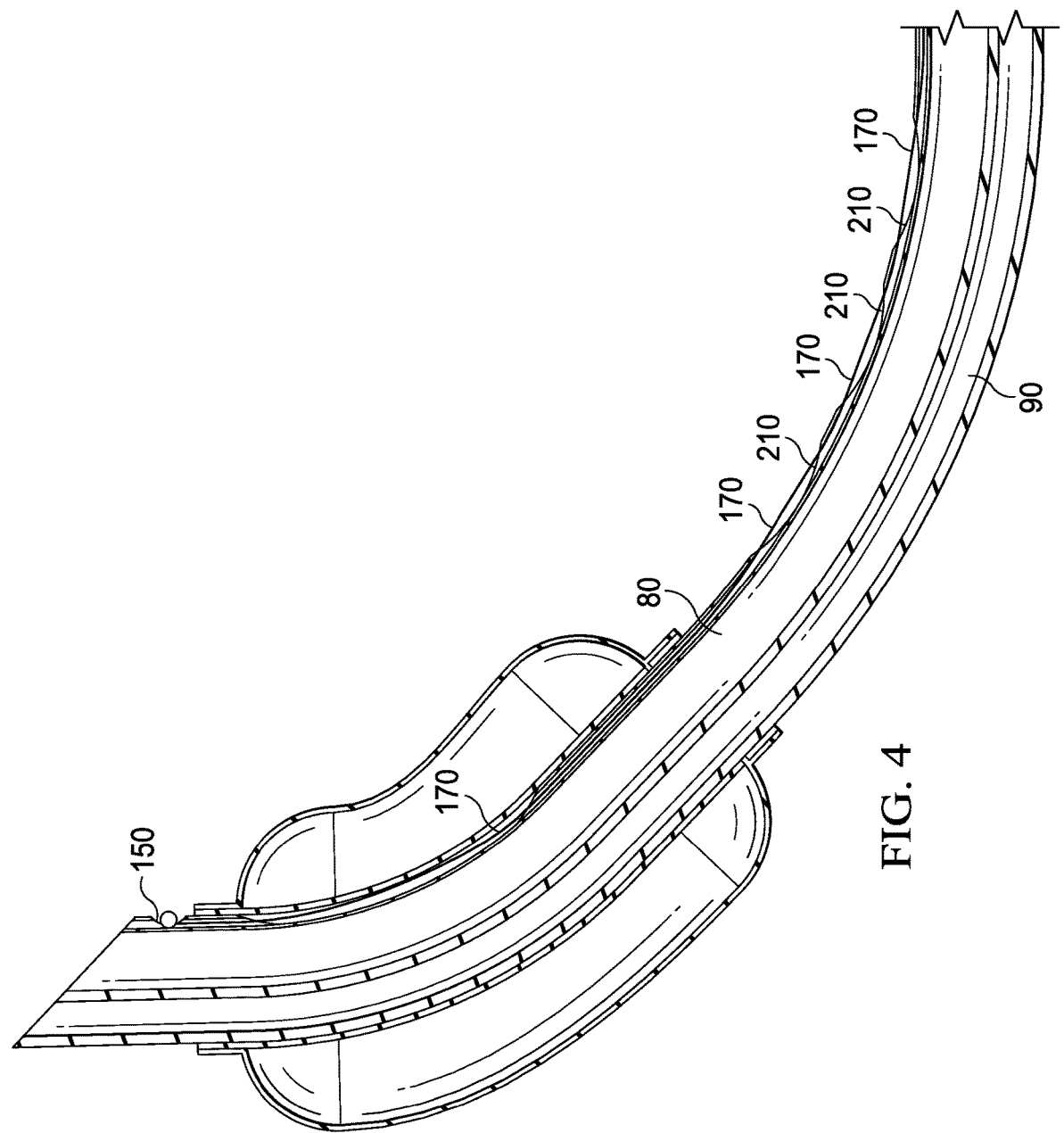
FIG. 4 is a cross sectional view of the distal portion of the exemplary embodiment shown in FIG. 3, with its shape adjusted by way of example only.

The tube 10 may include one or more cutouts 210 in the sidewall of tube 10. The cutouts 210 may extend along a portion of the length of the tube 10 and expose the wire 170 running through lumen 140. The number of cutouts 210, their placement along the length of the tube 10, and their shape may vary depending upon the desired shape of the tube 10 when the hub 100 is operated to modify the shape of tube 10. As collar 180 is moved along channel 200 toward the proximal end of tube 10, wire 170 which is secured to collar 180 will pull the distal end of tube 10 into a desired curved shape. The cutouts 210 contribute to the shaping of tube 10 by allowing the wire 170 to "bridge" the cutouts 210 in a straight-line fashion. See FIG. 4.

To prevent the escape of air from cuff 40, and to keep fluids and debris from reaching lumen 140 and wire 170, the cutouts 210 may be covered loosely with a cover 220 of a thin, flexible material, e.g., the material from which the cuff 40 is made.

In one exemplary embodiment an endotracheal tube 10 may be provided including a main tubular portion 70 including a distal end 30 and a proximal end 20 opposite the distal end, the main tubular portion 70 including a central lumen 80 at least in part defined by a wall of the main tubular portion 70; a wire lumen 140 disposed within the wall of the main tubular portion 70, the wire lumen 140 defined at least in part by a sidewall portion of the wire lumen 140 and extending from about the proximal end 20 of the main tubular portion 70 to about the distal end 30 of the main tubular portion 70; a wire 170 disposed in the wire lumen 140; and one or more cutouts 210 extending along a portion of the wall of the main tubular portion 70, the cutouts 210 comprising openings in the sidewall portion of the wire lumen 140, wherein the cutouts 210 are not in fluid communication with the central lumen 80. Each cutout 210 may be covered by a flexible material. An optics lumen 90 may extend along the length of the central lumen 80. In one embodiment, the optics lumen 90 may be disposed within the wall of the main tubular portion 70. In another embodiment, the optics lumen 90 may be disposed entirely within the wall of the main tubular portion. The optics lumen 90 may include a camera and/or a fiber optic cable. The proximal end of the wire 170 may be connected to a hub 100. The hub 100 may include a collar 180 moveable along a length of the hub 100, and the proximal end of the wire 170 may be coupled to the collar 180.

A cuff 40 may be disposed about the main tubular portion 70 proximate the distal end 30 of the main tubular portion 70; and one or more cutouts 210 may be disposed within the interior of the cuff 40. A flexible covering may be disposed over one or more of the cutouts 210 disposed within the interior of the cuff 40. In one embodiment, the cuff 40 and the flexible coverings are made of the same material.

In an alternate embodiment, the endotracheal tube may include one or more wires extending through one or more lumens in the wall of the endotracheal tube. Alternately, the lumens may be disposed along the length of the wall of the endotracheal tube. The wires extend from the distal end of the endotracheal tube to a hub located proximate the proximal end of the endotracheal tube. The hub advantageously slides along a portion of the length of the endotracheal tube. The hub also may rotate about the tube. The hub removably engages with a locking mechanism near the proximal end of the endotracheal tube. When engaged and locked, the hub adjusts the wires to force the endotracheal tube into a desired curved shape. By releasing the hub from the locking mechanism, the endotracheal tube assumes a relatively straighter shape.

In an alternate embodiment, one or more relatively rigid bands, e.g., stainless steel bands, may be positioned along the length of the endotracheal tube. The bands may differ in size and in shape depending upon their position along the tube. Also, bands may be fixed to the tube at the tip, or distal end, and may be moveable along the remainder of the tube's length. By flexing the tube into a desired position the bands may be locked into position to fix the tube into the desired position. The one or more wires also running along the length of the tube may be used to manipulate the tip of the tube to aid in insertion.

In an alternate embodiment, the tube may be preformed with one or more wedge-shaped segments of a relatively rigid material. The segments may be spaced apart by relatively flexible material, or may be joined together by hinge-like connections. When the hub is engaged, the wires may force the wedge-shaped segments to align next to one another, thus forming a desired endotracheal tube shape.

In another embodiment, one or more wires extend from the distal tip of the endotracheal tube to a more proximal position. Manipulating the one or more wires, e.g., by pushing, pulling, or twisting, at the proximal end effects a change in position of the distal tip of the endotracheal tube. In one embodiment, the wires are manipulated by bending the proximal end of the endotracheal tube, resulting in a desired tip movement.

In another exemplary embodiment, one or more lights are provided proximate the distal tip of the endotracheal tube. A first white LED light source may be provided at the distal tip to help with visualization during tube placement. A second red LED light source may be provided proximally to the tip, which when the tube is properly placed, would be visible to the intubating provider shining through the patient's skin, to help with tube placement. If placed incorrectly in the patient's esophagus, this light would be difficult to see.

At the distal tip of the endotracheal tube an LED light source may be provided. In one exemplary embodiment, the LED is a white LED. The light may be turned on as desired, e.g., with camera use. Where the tip of the endotracheal tube is beveled, the light may be positioned at either end of the bevel. However, positioning the light at the upper portion of the bevel—just slightly back from the lower bevel tip—may prove advantageous in helping to keep the tip free of fluids or debris.

Proximal from the distal tip of the endotracheal tube a second light source may be provided. The second light source in one exemplary embodiment includes a red transilluminating light to help visually confirm endotracheal tube placement. Advantageously, the second light source may be viewed through the patient's skin just below the Adam's apple. The second light source may be turned on or off as desired, e.g., with camera use. In some embodiments, placement of the second light proximal of an endotracheal tube inflatable cuff may prove helpful to ensure cuff placement just below the larynx.

In an alternate embodiment, either alone or in combination with one or more of the features described herein, an endotracheal tube includes a lumen within the body of the wall of the tube. A relatively stiff material, referred to herein for convenience only as a "dowel", may be disposed within the endotracheal tube wall lumen. The dowel may be adapted into a desired size and shape, and need not be circular in cross section. The dowel may be fixed to the endotracheal tube wall at its distal end proximate the distal end of the endotracheal tube. In one embodiment, the distal end of the dowel is fixed in place approximately one inch from the distal end of the endotracheal tube. The proximal end of the dowel remains free-floating within the endotracheal tube wall lumen. In one embodiment, the proximate end of the dowel is disposed approximately two inches from the proximal end of the endotracheal tube.

The endotracheal tube wall lumen may be formed with a notch therein approximately two inches from the proximal end of the endotracheal tube. The notch may be formed of such size and shape so as to be able to engage with the proximal end of the dowel. When the endotracheal tube is in a relatively straight, unflexed position, the dowel will extend from its fixed distal end to a point proximal the notch in the endotracheal tube wall. To flex the endotracheal tube into a desired configuration, one need simply bend the tube, which will cause the proximal end of the dowel to travel within the endotracheal tube wall lumen. When the tube is in a desired shape, the proximal end of the dowel engages the notch, e.g., by "snapping" into the notch. The dowel at this point may be under compression, and thus may hold the endotracheal tube in a desired shape.

The dowel may be formed of variable stiffness along its length. In that way, a desired shape of endotracheal tube may be accomplished. It is believed that having a thinner, or less stiff, section of dowel in a particular area will allow the endotracheal tube to flex more and assume a more curved shape proximate such area.

Another option for a stiffening mechanism may be through the use of electro-active polymers. Such polymers change shape when an electric current is passed through them. The polymers may be designed to assume a predetermined, desired shape when activated. Alternately, the endotracheal tube may be manually flexed and shaped, and the polymers within the tube then may be activated to hold the desired shape. Such polymer materials may prove advantageous, for example, in forming a distal endotracheal tube tip that one may manipulate.

In one embodiment, the endotracheal tube wall may be formed with a button proximate the notch. By depressing the button, the dowel may be forced out of the notch and allowed to float freely within the endotracheal tube wall lumen. Alternately, the wall of the endotracheal tube may be sufficiently pliable that simply pressing on the wall proximate the notch has the effect of dislodging the dowel from the notch.

An endotracheal tube may have one or more notches in its endotracheal tube wall lumen, so as to permit the tube to assume multiple positions. In that way, the tube may also include a button corresponding to each notch.

In one embodiment, the described stiffening means may be combined with the described maneuverable tip means. A stiffening rod extends along the inner curvature length of the endotracheal tube from a fixed distal end proximate the distal tip of the endotracheal tube, to a proximal location near the proximal end of the endotracheal tube. A stopper is provided within the lumen for the stiffening rod. In one embodiment, the free end of the inner curvature stiffening rod engages with and pushes against the stopper when the outer curvature dowel engages a notch. By continuing to flex the endotracheal tube after the stiffening rod engages with the stopper, the stiffening rod will cause the tip of the endotracheal tube to move in the direction generally opposite the endotracheal tube flexing.

It should be understood that the foregoing description is only illustrative of the invention. Various alternatives and modifications can be devised by those skilled in the art having the benefit of this disclosure, without departing from the invention. Accordingly, the invention is intended to embrace all such alternatives, modifications and variances.

Certain exemplary embodiments of the disclosure may be described. Of course, the embodiments may be modified in form and content, and are not exhaustive, i.e., additional aspects of the disclosure, as well as additional embodiments, will be understood and may be set forth in view of the description herein. Further, while the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention.

What is claimed is:
1. An endotracheal tube including:
   a main tubular portion including a distal end and a proximal end opposite the distal end, the main tubular portion including a central lumen at least in part defined by a wall of the main tubular portion;

a wire lumen disposed within the wall of the main tubular portion of the endotracheal tube and extending from the proximal end of the main tubular portion to the distal end of the main tubular portion, the wire lumen defined at least in part by a first sidewall portion of the wire lumen and a second sidewall portion of the wire lumen, wherein the first sidewall portion of the wire lumen extends from the wire lumen to the central lumen, and wherein the second sidewall portion of the wire lumen extends from the wire lumen to an outermost side of the wall of the main tubular portion;

a wire disposed in the wire lumen of the endotracheal tube;

at least two cutouts in the second sidewall portion of the wire lumen but not in the first sidewall portion of the wire lumen, the at least two cutouts extending along a portion of the wall of the main tubular portion, the at least two cutouts defining openings in the second sidewall portion of the wire lumen, the at least two cutouts are not in fluid communication with the central lumen, and the at least two cutouts allow the wire to bridge the at least two cutouts when the main tubular portion of the endotracheal tube bends at the at least two cutouts; and a cuff disposed about the main tubular portion proximate the distal end of the main tubular portion, the cuff having an interior and an exterior, a first cutout of the at least two cutouts being disposed within the interior of the cuff; and a second cutout of the at least two cutouts being disposed exterior to the cuff between the proximal end of the main tubular portion and the cuff.

2. The endotracheal tube of claim 1, wherein each cutout is covered by a flexible material.

3. The endotracheal tube of claim 1 further comprising an optics lumen extending along a length of the central lumen.

4. The endotracheal tube of claim 3, wherein the optics lumen is disposed within the wall of the main tubular portion.

5. The endotracheal tube of claim 4, wherein the optics lumen is disposed entirely within the wall of the main tubular portion.

6. The endotracheal tube of claim 3, wherein the optics lumen includes a camera.

7. The endotracheal tube of claim 3, wherein the optics lumen includes a fiber optic cable.

8. The endotracheal tube of claim 1 further comprising a hub, the wire having a distal end and a proximal end, the proximal end of the wire extending exterior to the wire lumen near the proximal end of the main tubular portion and being connected to the hub at a position that is exterior to the main tubular portion.

9. The endotracheal tube of claim 8, wherein the hub includes a collar moveable along a length of the hub, and wherein the proximal end of the wire is coupled to the collar.

10. The endotracheal tube of claim 1 further including a flexible covering over the first cutout that is disposed within the interior of the cuff.

11. The endotracheal tube of claim 10, wherein the cuff and the flexible covering are made of the same material.

12. The endotracheal tube of claim 1, wherein a third of the at least two cutouts is disposed between the proximal end of the main tubular portion and the exterior of the cuff.

13. The endotracheal tube of claim 1, wherein each of the at least two cutouts has a length and the length of the first cutout that is disposed within the interior of the cuff is greater than the length of the second cutout that is disposed exterior to the cuff.

14. An endotracheal tube comprising:

a main tubular portion including a distal end, a proximal end opposite the distal end, a tubular side wall comprising an exterior surface and an interior surface, and a central lumen defined by the interior surface of the tubular side wall;

a wire lumen disposed within the tubular side wall and extending from the proximal end of the main tubular portion to the distal end of the main tubular portion;

a wire disposed in the wire lumen;

multiple openings extending from the exterior surface of the tubular side wall and terminating within the wire lumen; and a cuff disposed on the main tubular portion proximate the distal end of the main tubular portion, the cuff having an interior and an exterior, a first opening of the multiple openings being disposed within the interior of the cuff, and a second opening of the multiple openings being disposed exterior to the cuff between the proximal end of the main tubular portion and the cuff, a portion of the distal end of the endotracheal tube being moveable from a first position to a second curved position, the wire forming a straight line bridge across each opening when the endotracheal tube is in the second curved position.

15. The endotracheal tube of claim 14, wherein at least two of the multiple openings are disposed between the proximal end of the main tubular portion and the exterior of the cuff.

16. The endotracheal tube of claim 15 further comprising an optics lumen extending along a length of the central lumen.

17. The endotracheal tube of claim 16, wherein the optics lumen is disposed within the wall of the main tubular portion.

18. The endotracheal tube of claim 17 further comprising an optical component positioned in the optics lumen, the optical component comprising a camera, a fiber optic cable, or a combination thereof.

19. The endotracheal tube of claim 14, wherein each of the multiple openings is covered by a flexible material.

20. The endotracheal tube of claim 14 further comprising a hub, the wire having a distal end and a proximal end, the proximal end of the wire extending exterior to the wire lumen near the proximal end of the main tubular portion and being connected to the hub at position that is exterior to the main tubular portion.

21. The endotracheal tube of claim 14, wherein each of the multiple openings has a length and the length of the first opening is greater than the length of the second opening.

22. An endotracheal tube comprising:

a main tubular portion including a distal end, a proximal end opposite the distal end, a tubular side wall comprising an exterior surface and an interior surface, and a central lumen defined by the interior surface of the tubular side wall;

a wire lumen disposed within the tubular side wall and extending from the proximal end of the main tubular portion to the distal end of the main tubular portion;

a first wire disposed in the wire lumen;

multiple openings extending from the exterior surface of the tubular side wall and terminating within the wire lumen, each of the multiple openings being covered by a flexible material;

an optics lumen disposed within the wall of the main tubular portion;

an optical component positioned in the optics lumen, the optical component comprising a second wire, a camera, a fiber optic cable, or a combination thereof; and a cuff positioned on the main tubular portion proximate the distal end of the main tubular portion, the cuff having an interior and an exterior, one of the multiple openings being disposed within the interior of the cuff, and at least two of the multiple openings being disposed exterior to the cuff between the proximal end of the main tubular portion and the cuff, a portion of the distal end of the endotracheal tube being moveable from a first position to a second curved position, the first wire forming a straight-line bridge across each opening when the endotracheal tube is in the second curved position.

\* \* \* \* \*